US010464958B2

(12) United States Patent
Notte et al.

(10) Patent No.: US 10,464,958 B2
(45) Date of Patent: *Nov. 5, 2019

(54) METHOD FOR THE SYNTHESIS OF ALPHA-AMINOALKYLENEPHOSPHONIC ACID

(71) Applicant: Monsanto Technology LLC, St. Louis, MO (US)

(72) Inventors: Patrick Notte, Wavre (BE); Samuel Cogels, Brussels (BE); Sebastian Burck, Louvain-la-Neuve (BE)

(73) Assignee: Monsanto Technology LLC, St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/848,219

(22) Filed: Dec. 20, 2017

(65) Prior Publication Data

US 2018/0346497 A1     Dec. 6, 2018

Related U.S. Application Data

(63) Continuation of application No. 14/415,688, filed as application No. PCT/EP2013/065124 on Jul. 17, 2013, now abandoned.

(30) Foreign Application Priority Data

Jul. 17, 2012  (EP) .................................... 12176757

(51) Int. Cl.
C07F 9/6533    (2006.01)
C07F 9/572     (2006.01)
C07F 9/6524    (2006.01)
C07F 9/38      (2006.01)

(52) U.S. Cl.
CPC .......... C07F 9/6533 (2013.01); C07F 9/3808 (2013.01); C07F 9/3813 (2013.01); C07F 9/3873 (2013.01); C07F 9/3886 (2013.01); C07F 9/572 (2013.01); C07F 9/5728 (2013.01); C07F 9/6524 (2013.01)

(58) Field of Classification Search
None
See application file for complete search history.

(56) References Cited

U.S. PATENT DOCUMENTS

| 3,288,846 A | 11/1966 | Irani et al. |
| 3,451,937 A | 6/1969 | Quimby |
| 3,455,675 A | 7/1969 | Irani et al. |
| 3,796,749 A | 3/1974 | Krueger et al. |
| 3,799,758 A | 3/1974 | Franz |
| 3,816,517 A | 6/1974 | Krueger et al. |
| 3,832,393 A | 8/1974 | Krueger et al. |
| 3,927,080 A | 12/1975 | Gaertner |
| 3,959,361 A * | 5/1976 | Krueger ................ C07F 9/3817 562/12 |
| 3,969,398 A | 7/1976 | Hershman |
| 4,065,491 A | 12/1977 | Pfliegel et al. |
| 4,211,547 A | 7/1980 | Gaertner |
| 4,237,065 A | 12/1980 | Ehrat |
| 4,400,330 A | 8/1983 | Wong et al. |
| 4,407,761 A | 10/1983 | Blum et al. |
| 4,422,982 A | 12/1983 | Subramanian |
| 4,617,415 A | 10/1986 | Balthazor et al. |
| 4,624,937 A | 11/1986 | Chou |
| 4,654,429 A | 3/1987 | Balthazor et al. |
| 4,657,705 A | 4/1987 | Miller et al. |
| 4,804,499 A | 2/1989 | Miller et al. |
| 4,931,585 A | 6/1990 | Pelyva et al. |
| 5,155,257 A | 10/1992 | Kleiner |
| 5,312,972 A | 5/1994 | Cullen |
| 5,312,973 A | 5/1994 | Donadello |
| 5,688,994 A | 11/1997 | Baysdon et al. |
| 7,084,298 B2 | 8/2006 | Maase et al. |
| 9,150,599 B2 | 10/2015 | Burck et al. |

(Continued)

FOREIGN PATENT DOCUMENTS

| CA | 1039739 | 10/1978 |
| CH | 275435 A | 5/1951 |

(Continued)

OTHER PUBLICATIONS

Reusch ("Properties of Phosphorus Compounds", downloaded from https://chem.libretexts.org/Textbook_Maps/Organic_Chemistry/Supplemental_Modules_(Organic_Chemistry)/Organo-phosphorus_Compounds/Properties_of_Phosphorus_Compounds on Nov. 15, 2018, p. 1-3) (Year: 2018).*

Phosphorus Pentoxide (Merck Index Entry, downloaded from https://www.rsc.org/Merck-Index/monograph/m8737/phosphorus%20pentoxide?q=authorize on Nov. 15, 2018, p. 1-3) (Year: 2018).*

Acetic Anhydride (downloaded from https://www.sigmaaldrich.com/catalog/product/sial/320102?lang=en&region=US on Nov. 15, 2018, p. 1-6) (Year: 2018).*

(Continued)

Primary Examiner — Amy C Bonaparte
(74) Attorney, Agent, or Firm — Stinson LLP; Erin C. Robert

(57) ABSTRACT

The present invention is related to a new method for the synthesis of alpha-aminoalkylenephosphonic acid or its phosphonate esters comprising the steps of forming a reaction mixture by mixing a P—O—P anhydride moiety comprising compound, having one P-atom at the oxidation state (+III) and the other P-atom at the oxidation state (+III) or (+V), an aminoalkanecarboxylic acid and an acid catalyst, wherein said reaction mixture comprises an equivalent ratio of alpha-aminoalkylene carboxylic acid to P—O—P anhydride moieties of at least 0.2, and recovering the resulting alpha-aminoalkylene phosphonic acid compound or an ester thereof from the reaction mixture.

20 Claims, No Drawings

(56) References Cited

U.S. PATENT DOCUMENTS

| | | |
|---|---|---|
| 2004/0024180 A1 | 2/2004 | Drauz et al. |
| 2011/0118502 A1 | 5/2011 | Notte et al. |
| 2011/0264267 A1* | 10/2011 | Schipper ............... C01B 25/12 700/268 |
| 2015/0166584 A1 | 6/2015 | Devaux et al. |
| 2015/0232493 A1 | 8/2015 | Notte et al. |

FOREIGN PATENT DOCUMENTS

| | | |
|---|---|---|
| CH | 620223 | 11/1980 |
| CN | 1631894 | 6/2005 |
| CN | 1285600 | 11/2006 |
| DE | 3903715 | 8/1989 |
| DE | 3903716 | 8/1989 |
| DE | 4026026 | 2/1992 |
| DE | 19909200 | 3/2000 |
| DE | 19914375 | 10/2000 |
| EP | 0480307 A2 | 4/1992 |
| EP | 0537786 A1 | 4/1993 |
| EP | 0595598 A1 | 5/1994 |
| EP | 0638577 A1 | 2/1995 |
| EP | 1681294 A1 | 7/2006 |
| EP | 1681295 A1 | 7/2006 |
| EP | 2112156 A1 | 10/2009 |
| ES | 2018746 A6 | 5/1991 |
| GB | 1142294 A | 2/1969 |
| GB | 1230121 A | 4/1971 |
| GB | 2154588 A | 9/1985 |
| GB | 2154589 A | 9/1985 |
| IN | 192483 | 4/2004 |
| JP | 5775990 A | 5/1982 |
| JP | 2007022956 A | 2/2007 |
| RO | 101476 A2 | 12/1991 |
| RU | 2402558 C2 | 10/2010 |
| WO | 9415939 A1 | 7/1994 |
| WO | 9422880 A1 | 10/1994 |
| WO | 9640698 A1 | 12/1996 |
| WO | 9819992 A1 | 5/1998 |
| WO | 9835930 A1 | 8/1998 |
| WO | 0002888 A1 | 1/2000 |
| WO | 0009520 A1 | 2/2000 |
| WO | 0014093 A1 | 3/2000 |
| WO | 0192208 A1 | 12/2001 |
| WO | 02055527 A1 | 7/2002 |
| WO | 2006107824 A2 | 10/2006 |
| WO | 2009068636 A1 | 6/2009 |
| WO | 2009130322 A1 | 10/2009 |
| WO | 2010055056 A1 | 5/2010 |
| WO | 2010136566 A1 | 12/2010 |
| WO | 2010136574 A1 | 12/2010 |
| WO | 2011039378 | 4/2011 |
| WO | 2011051309 A1 | 5/2011 |

OTHER PUBLICATIONS

Boroujeni, "Synthesis of a-Aminophosphonates Using Polystyrene Supported Al(Olf)3 as a Heterogeneous Catalyst", Synthesis and Reactivity in Inorganic, Matal-Organic, and Nano-Metal Chemistry 2011, vol. 41, pp. 173-176.

Corbridge, "4. Phosphides of Non-Metals", Phosphorus Chemistry, Biochemistry, and Technology, 6th Edition, D.E.C Corbridge, Ed, 2013, 118 Pages.

Merck Index (entry for nitrilotriacetic acid, downloaded from https://www.rsc.org/MerckIndex/monograph/m7935/nitrilotriacetic%20acid?q=authorize on Jun. 10, 2017).

Greenwood, "Phosphorus Oxides, Sulfides, Selenides and Related compounds", Chemistry of the Elements, 2nd ed., Chapter 123.5, 1998, pp. 503-510.

International Search Report for PCT/EP2013/065124, Completed by the European Patent Office dated Sep. 11, 2013, 3 pages.

European Search Report for European Application No. 12176757, Completed by the European Patent Office dated Jan. 9, 2013, 4 pages.

Arizpe et al., "Stereodivergent synthesis of two a-aminophosphonic acids characterized by a cis-fused octahydroindole system" Eur. J. Org. Chem. 2011, pp. 3074-3081.

Tapia-Benavidis et al., "Syntheses of N-Substituted 2,5-Piperazindiones", Heterocycles 1997, vol. 45, pp. 1679-1686.

* cited by examiner

METHOD FOR THE SYNTHESIS OF ALPHA-AMINOALKYLENEPHOSPHONIC ACID

REFERENCE TO RELATED APPLICATIONS

This application is a continuation of U.S. patent application Ser. No. 14/415,688, filed Jan. 19, 2015, which is a U.S. National Stage Application of International Patent Application No. PCT/EP2013/065124, filed Jul. 17, 2013, which claims the benefit of European Application No. 12176757.8, filed Jul. 17, 2012, the entire contents of each of which are incorporated herein by reference.

FIELD OF THE INVENTION

The present invention is related to a method for the synthesis of alpha-aminoalkylenephosphonic acid or its phosphonate esters.

STATE OF THE ART

Alpha-amino-phosphonic acid compounds are well known in the art and have found widespread commercial acceptance for a variety of applications including water-treatment, scale-inhibition, detergent additives, sequestrants, marine-oil drilling adjuvants, ion exchange when grafted on resins and as pharmaceutical components. It is well known that such applications preferably require amino alkylenephosphonic acids wherein a majority of the nitrogen substituents are alkylenephosphonic acid groups.

There are several ways for producing alpha-aminoalkylenephosphonic acid such as those which are for example disclosed in GB 1142294, GB 1230121, U.S. Pat. No. 3,288,846, JP 57075990, U.S. Pat. No. 3,832,393, EP 1681294, EP 1681295 and EP 0638577 patents and in WO 96/40698, JP2007022956 and WO 2009/130322 patent applications among others.

U.S. Pat. No. 3,796,749 discloses a process for producing substantially pure aminomethylenephosphonic acids in a high yield, comprising reacting N-substituted alpha-amino mono- or polycarboxylic acids or their alkali metal salts with phosphorous acid in the presence of water-binding agents at a temperature between about 90° C. and about 160° C. Suitable water-binding agents are acid anhydrides which, by combination with water, are converted into the corresponding acids. Such agents are, for instance, lower alkanoic acid anhydrides such as acetic acid anhydride, propionic acid anhydride, or inorganic acid anhydrides such as phosphorus pentoxide and the like.

U.S. Pat. No. 3,816,517 discloses a method for the preparation of substantially pure aminomethylenephosphonic acids in a high yield by reacting N-substituted alpha-amino mono- or polycarboxylic acids or their alkali metal salts with phosphorous acid and/or phosphorus trihalogenide, preferably phosphorus trichloride in the presence or absence of an inert diluents. If no phosphorous acid and only phosphorus trichloride is used, a certain amount of water is added to the phosphorus trichloride to form phosphorous acid so that a mixture of phosphorus trichloride and phosphorous acid is present in the reaction mixture. The reaction can also be carried out with phosphorous acid alone. In general, phosphorous acid and/or phosphorus trihalogenide are added to the alpha-aminomethylenecarboxylic acid.

IN 192483 patent discloses a process for the preparation of ethylene diamine tetra-(methylene phosphonic acid) by reacting ethylenediamino tetra-(acetic acid) with phosphorus trichloride and phosphorous acid.

U.S. Pat. No. 3,451,937 claims for a detergent composition consisting essentially of (A) a water soluble organic detergent and (B) ethanehydroxytriphosphonic acid or a salt thereof. In column 4, lines 60 to 75, the reaction of phosphonoacetic acid (2 moles) with tetraphosphorus hexaoxide (1 mole) is disclosed, with a C:P atomic ratio of the reaction system of 4:6 where ethane-1-hydroxy-1,1,2-triphosphonic acid is produced with a high yield.

EP 2112156 patent application discloses a method for the manufacture of aminoalkylene phosphonic acid, comprising the steps of adding tetraphosphorus hexaoxide to an aqueous reaction medium containing a homogeneous Brønsted acid, whereby the tetraphosphorus hexaoxide will substantially qualitatively hydrolyse to phosphorous acid, whereby the free water level in the reaction medium, after the hydrolysis of the tetraphosphorus hexaoxide is completed, is in the range of from 0 to 40% by weight. In a subsequent step an amine, formaldehyde and additional Brønsted acid is added to the reaction medium whereupon the reaction is completed to thus yield the aminoalkylene phosphonic acid In a variant of this process, the amine can be added before or during the tetraphosphorus hexaoxide hydrolysis step.

The art is thus, as one can expect, crowded and is possessed of methods for the manufacture of such compounds. The state-of-the-art manufacture of alpha-aminoalkylenephosphonic acids is premised on converting phosphorous acid resulting from the hydrolysis of phosphorus trichloride or on converting phosphorous acid via the addition of hydrochloric acid which hydrochloric acid can be, in part or in total, added in the form of an amine hydrochloride.

The actual technology, based on the phosphorus trichloride hydrolysis is subject to well known deficiencies ranging from the presence of hydrochloric acid to losses of phosphorus trichloride due to volatility and entrainement by hydrochloric acid. In addition, the control of the reaction temperature is critical to limit phosphorus trichloride losses (bp. 76° C.) and to avoid the formation of low oxides of phosphorus which creates safety concerns.

Further processes for preparing aminomethylenephosphonic acids wherein amines are reacted with an aldehyde or ketone and a compound of trivalent phosphorus, such as phosphorous acid, esters of phosphorous acid, or phosphorus trihalide, in general are characterized by rather low yields which usually do not exceed about 55% to 60%. These low yields are due to the formation of by-products, as well as end products with different degrees of alkylenephosphonic acid substitution. Separation and purification thus becomes a difficult and cumbersome task.

Therefore, a need exists to obtain alpha-aminoalkylenephosphonic acid compounds by technologically new, but also economically acceptable routes in a superior manner consonant with standing desires.

From the above, it is entirely unexpected that a carboxyl group of an alpha-aminoalkylenecarboxylic acid can be replaced by a phosphonic acid group through the reaction of the alpha-aminoalkylenecarboxylic acid with tetraphosphorus hexaoxide. On the contrary, as it is for example disclosed in U.S. Pat. No. 3,451,937, the carboxyl group reacts with the tetraphosphorus hexaoxide in an entirely different manner.

AIMS OF THE INVENTION

The present invention aims to provide a new and efficient synthesis of alpha-aminoalkylenephosphonic acid or its phosphonate esters that does not present the drawbacks of the methods of the prior art. It is another aim of this invention to provide a one step synthesis method capable of selectively delivering superior compound grades at high purity and high yield. Yet another aim of the present invention is to synthesize the phosphonic acid compounds in a shortened and energy efficient manner.

SUMMARY OF THE INVENTION

The present invention discloses a method for the synthesis of an alpha-aminoalkylenephosphonic acid or an ester thereof comprising the steps of:
 a) forming a reaction mixture by mixing a compound comprising one or more P—O—P anhydride moieties, said moieties comprising one P-atom at the oxidation state (+III) and the other P-atom at the oxidation state (+III) or (+V), an alpha-aminoalkylenecarboxylic acid and an acid catalyst, wherein
  said compound comprising one or more P—O—P anhydride moieties is selected from the group consisting of:
  tetraphosphorus hexaoxide, tetraethylpyrophosphite, a compound obtained from the combination of one or more compounds comprising one or more P—OH moieties with one or more compounds comprising one or more P—O—P anhydride moieties, wherein the P atom of one or more compounds is at the oxidation state (+III) and wherein the compounds having one or more P—OH moieties are accessible by tautomerization of a >P(=O)H moiety; and a compound obtained from the combination of one or more compounds having 2 or more P—O—P moieties and water, wherein the P—O—P moieties have one P atom at the oxidation state (+III) and one P-atom at the oxidation state (+III) or (+V);
  and wherein
  said reaction mixture comprises an equivalent ratio of alpha-aminoalkylenecarboxylic acid to P—O—P anhydride moieties of at least 0.2,
  and
 b) recovering the resulting alpha-aminoalkylenephosphonic acid compound or an ester thereof from said reaction mixture.

Preferred embodiments of the present invention disclose one or more of the following features:
 the reaction mixture is formed by gradually adding a P—O—P anhydride moiety comprising compound, having one P-atom at the oxidation state (+III) and the other P-atom at the oxidation state (+III) or (+V), to a mixture comprising an alpha-aminoalkanecarboxylic acid and an acid catalyst;
 the reaction mixture is formed by gradually adding a mixture comprising an alpha-aminoalkanecarboxylic acid and an acid catalyst to a P—O—P anhydride moiety comprising compound, having one P-atom at the oxidation state (+III) and the other P-atom at the oxidation state (+III) or (+V);
 the method for the synthesis of an alpha-aminoalkylenephosphonic acid or an ester thereof comprises the additional steps of:
  adding water to the reaction mixture after completion of the conversion of alpha-aminoalkylene carboxylic acid into alpha-aminoalkylene phosphonic acid;
  bringing the reaction mixture comprising the added water, to a temperature comprised between 20° C. and 100° C. and
  maintaining the reaction mixture comprising the added water at said temperature for at least 10 minutes;
 the P—O—P anhydride moiety comprising compound is selected from the group consisting of tetraphosphorus hexaoxide, tetraethylpyrophosphite, and the P—O—P anhydride moiety comprising compound obtained from the combination of phosphorous acid and tetraphosphorus hexaoxide, of phosphorous acid and tetraphosphorus decaoxide, of dimethylphosphite and tetraphosphorus decaoxide and of tetraphosphorus hexaoxide and water;
 the P—O—P anhydride moiety comprising compound is tetraphosphorus hexaoxide; the alpha-aminoalkylene carboxylic acid comprising compound has the general formula:

$R^1$—$N(R^2)$—$CR^3R^4$—$CO_2M$ wherein $R^1$ can be a substituted C or substituted S atom; $R^2$ can be a H atom, a substituted C or a substituted S atom; $R^3$ and $R^4$ can be independently a H atom or a substituted C atom: M can be a H atom or an alkaline or alkaline earth metal;
 the alpha-aminoalkylene carboxylic acid comprising compound is selected from
  a) a compound wherein the N atom possesses a low basicity by substitution of the N atom with electron withdrawing groups or groups that are able to partly delocalise the N-lone pair;
  b) a polyamine wherein at least two N atoms are present and each N atom is separated by at least two carbon atoms from the next neighbouring N atom;
  c) a compound wherein the N atom is substituted by alkyl groups; the alpha-aminoalkylene carboxylic acid comprising compound is selected from
  a) nitrilotriacetic acid, ethylenediaminetetraacetic acid, diethylenetriaminepentaacetic acid, N-benzyliminodiacetic acid, N-methyliminodiacetic acid, iminodiacetic acid, N,N-bis(carboxymethyl)-1-glutamic acid, trisodium-N,N-bis(carboxymethyl)-alanine, N-cyanomethyl alanine, N,N-bis(cyanomethyl)-glycine, 4-morpholinoacetic acid, pyroglutamic acid, N-acetyl glycine, N,N-bis(carboxymethyl)-6-aminohexanoic acid, N-phenyl glycine, N-tosyl glycine, trans-1,2-cyclohexyldiaminotetraacetic acid monohydrate, N-phosphonomethyliminodiactic acid, iminodiacetic acid grafted on resin such as for example acidified Amberlite IRC748i;
  b) 1,4,7,10-tetraazadodecane-1,4,7,10-tetraacetic acid, trans-1,2-cyclohexyldiaminotetracetic acid monohydrate;
  c) N,N'-dimethylglycine.
 the acid catalyst is a homogeneous Brønsted acid catalyst preferably selected from the group consisting of methanesulfonic acid, trifluoromethanesulfonic acid, acetic acid, trifluoroacetic acid, p-toluenesulfonic acid, hydrochloric acid, phosphorous acid, phosphoric acid and mixtures thereof.
 the acid catalyst is a heterogeneous Brønsted acid catalyst selected from the group consisting of:
  (i) solid acidic metal oxide combinations as such or supported onto a carrier material;
  (ii) cation exchange resins selected from the group comprising copolymers of styrene, ethylvinyl benzene and divinyl benzene, functionalized so as to graft $SO_3H$ moieties onto the aromatic group and perfluorinated resins carrying carboxylic and/or sulfonic acid groups;
  (iii) organic sulfonic, carboxylic and phosphonic Brønsted acids (which are substantially immiscible in the reaction medium at the reaction temperature);
  (iv) an acid catalyst derived from:
   the interaction of a solid support having a lone pair of electrons onto which is deposited an organic Brønsted acid; or the interaction of a solid support having a lone pair of electrons onto which is deposited a compound having a Lewis acid site; or heterogeneous solids functionalized by chemical grafting with a Brønsted acid group or a precursor therefore; and (v) heterogeneous heteropolyacids of the general formula $H_xPM_yO_z$ wherein P is selected from phosphorus and silicon and M is selected from tungsten and molybdenum and combinations thereof.

the acid catalyst is a Lewis acid catalyst selected from the group consisting of $LiN(CF_3SO_2)_2$, $Mg(OCF_3SO_2)_2$, $Al(OCF_3SO_2)_3$, $Bi(OCF_3SO_2)_3$, $Sc(OCF_3SO_2)_3$.

the reaction mixture comprises a diluent selected from the group consisting of 1,4-dioxane, toluene, ethylacetate, sulfolane, acetonitrile, 1-ethyl-3-methyl-imidazolium bis(trifluoromethylsulfonyl)imide, or a mixture thereof.

the equivalent ratio of alpha-aminoalkylenecarboxylic acid to P—O—P anhydride moiety is comprised between 0.2 and 4.5, preferably between 0.3 and 3.0, more preferably between 0.3 and 2.5 and most preferably between 0.5 and 1.5.

the ratio of the alpha-aminoalkylenecarboxylic acid equivalents to the moles of tetraphosphorus hexaoxide is comprised between 1.0 and 12.0, preferably between 1.0 and 10.0, more preferably between 1.5 and 8.0 and most preferably between 2.0 and 6.0.

the ratio of the moles of acid catalyst to the alpha-aminoalkylenecarboxylic acid equivalents is comprised between 0.01 and 11.0, preferable between 0.01 and 10.0, more preferably between 0.1 and 9.0, even more preferably between 1.0 and 7.0 and most preferably between 2.0 and 5.0.

the P—O—P anhydride moiety comprising compound is mixed with the mixture of alpha-aminoalkylene carboxylic acid and acid catalyst, at a temperature comprised between 20° C. and 120° C., preferably between 20° C. and 80° C.

the reaction mixture, after completion of the mixing, is maintained at a temperature comprised between 20° C. and 100° C., preferably between 40° C. and 90° C. and more preferably between 50° C. and 80° for a period of time comprised between 10 minutes and 72 hours.

the reaction mixture, after completion of the P—O—P anhydride moiety comprising compound addition, is maintained at a temperature comprised between 20° C. and 100° C., preferably between 40° C. and 90° C. and more preferably between 50° C. and 80° for a period of time comprised between 10 minutes and 72 hours.

the obtained alpha-aminoalkylenephosphonic acid is selected from the group consisting of aminomethylphosphonic acid, (N,N-dimethylamino)methylphosphonic acid, phthalimidomethylphosphonic acid, N-phenyl-aminomethylphosphonic acid, N-tosyl-aminomethylphosphonic acid, N-phosphonomethylglycine, phosphonomethyliminodiacetic acid, 4-morpholinemethylphosphonic acid, 4-amino-4-phosphonobutyric acid, 5-phosphono-2-pyrrolidone, N,N-bis(phosphonomethyl)-6-amino-hexanoic acid, N,N-bis(phosphonomethyl)-4-amino-4-phosphono-butyric acid, N,N-bis(phosphonomethyl)-4-amino-glutamic acid, N,N-bis(phosphonomethyl)-1-amino-ethyl-phosphonic acid, imino (bismethylenephosphonic acid), N-methyl-imino (bismethylenephosphonic acid), N-benzyl-imino (bismethylenephosphonic acid), aminotrismethylenephosphonic acid, ethylene diamino tetra-(methylene phosphonic acid), trans-1,2-cyclohexyldiaminotetramethylenephosphonic acid, 1,4,7,10-tetraazadodecane-1,4,7, 10-tetramethylenephosphonic acid, N-methyl-iminodiphosphonic acid.

carbon monoxide, formed in the reaction of the P—O—P anhydride moiety comprising compound and the alpha-aminoalkylene carboxylic acid, is recovered and reused.

alpha-aminoalkylenephosphonic acid or its esters, obtained by the method of the present invention, are used as scale inhibitor, dispersing agent, sequestering agent, detergent additive, marine-oil drilling adjuvant, pharmaceutical component, for ion exchange when grafted on an organic or inorganic support, as ligands to immobilize homogeneous metallic catalysts and as heterogeneous acid catalysts.

DETAILED DESCRIPTION OF THE INVENTION

The present invention provides an efficient and economical method for the synthesis of alpha-aminoalkylenephosphonic acid or its phosphonate esters with high selectivity and high yield wherein the phosphonate esters comprise one or more substituted or unsubstituted hydrocarbyl groups which may be branched or unbranched, saturated or unsaturated and may contain one or more rings. Suitable hydrocarbyls include alkyl, alkenyl, alkynyl and aryl moieties. They also include alkyl, alkenyl, alkynyl and aryl moieties substituted with other aliphatic or cyclic hydrocarbyl groups, such as alkaryl, alkenaryl and alkynaryl.

The substituted hydrocarbyl is defined as a hydrocarbyl wherein at least one hydrogen atom has been substituted with an atom other than hydrogen such as an halogen atom, an oxygen atom to form for example an ether or an ester, a nitrogen atom to form an amide or nitrile group or a sulfur atom to form for example a thioether group.

Phosphonate esters in general are prepared by using the P—O—P anhydride moiety comprising compound substituted with the corresponding hydrocarbyl substituents.

The present method includes an arrangement whereby a P—O—P anhydride moiety comprising compound, having one P-atom at the oxidation state (+III) and the other P-atom at the oxidation state (+III) or (+V), and an alpha-aminoalkylenecarboxylic acid are reacted in the presence of an acid catalyst and optionally a diluent.

While the P—O—P anhydride moiety comprising compound is preferably selected from the group consisting of tetraphosphorus hexaoxide and partially hydrolysed species of tetraphosphorus hexaoxide obtained through reaction of 1 mole of tetraphosphorus hexaoxide with 1, 2, 3, 4 and 5 moles of water respectively, it is understood that all compounds comprising at least one P—O—P anhydride moiety wherein one P-atom is at the oxidation state (+III) and the other P-atom is at the oxidation state (+III) or (+V) can be used for the purpose of the invention.

Suitable P—O—P anhydride moiety comprising compounds can either comprise a P—O—P anhydride moiety in the compound itself (e.g. $P_4O_6$ or pyrophosphites $(RO)_2P—O—P(OR)_2$) or be generated in situ by combining reagents that will form the required P—O—P anhydride moiety upon combination before reacting with the alpha-aminoalkylene carboxylic acid.

Suitable reagent combinations are a) compounds containing a least one P—OH moiety (also accessible by tautomerisation of a >P(=O)H moiety into >P(LP)OH (where LP stands for lone pair of electrons) as possible for dimethylphosphite $(MeO)_2P(=O)H)$ and compounds containing at least one P—O—P anhydride moiety e.g. $P_2O_5$ or $P_4O_6$ and b) partial hydrolysis of a compound containing P—O—P anhydride moieties. In case a it is mandatory that at least in one of the utilised compounds the P-atom is at the oxidation state (+III) whereas in case b) the P—O—P moieties have one P atom at the oxidation state (+III) and the other P-atom at the oxidation state (+III) or (+V), in order to form the P—O—P anhydride moiety comprising compound, having one P-atom at the oxidation state (+III) and the other P-atom at the oxidation state (+III) or (+V).

P—O—P anhydride moiety comprising compounds wherein the P—O—P anhydride moiety is already present are phosphorus oxides with the formula $P_4O_n$ with n=6-9, pyrophosphites with the general formula $(RO)_2P$—O—P $(OR)_2$ wherein R is an alkyl or aryl group, pyrophosphorous acid $(H_4P_2O_5)$, and isohypophosphoric acid $(H(HO)P(O)$—O—$P(O)(OH)_2)$.

Combinations described under a) are obtained by reacting e.g. phosphorus oxides with formula $P_4O_n$ with n=6-10; alkyl substituted pyrophosphites, pyrophosphorous acid, isohypophosphoric acid, metaphosphoric acid or polyphosphoric acid with phosphorous acid, phosphoric acid, mono or disubstituted phosphites with formula $(RO)PO_2H_2$ or $(RO)_2POH$ wherein R is an alkyl or aryl group, phosphate esters $(RO)PO_3H_2$ or $(RO)_2PO_2H$, phosphonic acids or its monoester $RPO_3H_2$ or $RPO_2H(OR)$ with the proviso that such combinations will lead to P—O—P anhydride moiety comprising compound having one P-atom at the oxidation state (+III) and the other P-atom at the oxidation state (+III) or (+V).

Most preferred are tetraphosphorus hexaoxide, tetraethylpyrophosphite and the combinations of phosphorous acid and tetraphosphorus hexaoxide, of phosphorous acid and tetraphosphorus decaoxide, of dimethylphosphite and tetraphosphorus decaoxide and of tetraphosphorus hexaoxide and water.

The amount of 'reactive' P(+III) atoms that can be converted into phosphonic acids according to this invention is determined by the amount of P(+III) atoms and the amount of P—O—P anhydride moieties. If there are more P—O—P anhydride moieties than P(+III) atoms then all P(+III) atoms are converted into phosphonic acids. If there are less P—O—P anhydride moieties than P(+III) atoms then only a part of P(+III) atoms, equal to the amount of P—O—P anhydride moieties, is converted into phosphonic acids.

The tetraphosphorus hexaoxide preferably used within the scope of the present invention may be represented by a substantially pure compound containing at least 85%, preferably more than 90%, more preferably at least 95% and in one particular execution at least 97% of $P_4O_6$. While tetraphosphorus hexaoxide, suitable for use within the context of this invention, may be manufactured by any known technology, in preferred executions it is prepared in accordance with the method described in WO 2009/068636 and/or WO 2010/055056 patent applications under the section entitled "Process for the manufacture of $P_4O_6$ with improved yield". In detail, oxygen, or a mixture of oxygen and inert gas, and gaseous or liquid phosphorus are reacted in essentially stoichiometric amounts in a reaction unit at a temperature in the range from 1600 K to 2000 K, by removing the heat created by the exothermic reaction of phosphorus and oxygen, while maintaining a preferred residence time of from 0.5 seconds to 60 seconds followed by quenching the reaction product at a temperature below 700 K and refining the crude reaction product by distillation. The tetraphosphorus hexaoxide so prepared is a pure product containing usually at least 97% of the oxide. The so produced $P_4O_6$ is generally represented by a liquid material of high purity containing in particular low levels of elementary phosphorus, $P_4$, preferably below 1000 ppm, expressed in relation to the $P_4O_6$ being 100%. The preferred residence time is from 5 seconds to 30 seconds, more preferably from 8 seconds to 30 seconds. The reaction product can, in one preferred execution, be quenched to a temperature below 350 K.

It is presumed that the $P_4O_6$ participating in a reaction at a temperature of from 24° C. (melting t°) to 120° C. is necessarily liquid or gaseous although solid species can, academically speaking, be used in the preparation of the reaction medium.

For reasons of convenience and operational expertise, the tetraphosphorus hexaoxide, represented by $P_4O_6$, is of high purity and contains very low levels of impurities, in particular elemental phosphorus, $P_4$, at a level below 1000 ppm, usually below 500 ppm and preferably not more than 200 ppm, expressed in relation to the $P_4O_6$ being 100%.

The alpha-aminoalkylene carboxylic acid comprising compound, used in the present invention, can be a molecule, a polymer, a resin or an organic molecule or polymer grafted on an inorganic material and may be represented by the general formula:

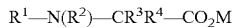

$$R^1\text{—}N(R^2)\text{—}CR^3R^4\text{—}CO_2M$$

wherein $R^1$ can be a substituted C or substituted S atom; $R^2$ can be a H atom, a substituted C or a substituted S atom; $R^3$ and $R^4$ can be independently a H atom or a substituted C atom: M can be a H atom or an alkaline or alkaline earth metal.

Preferably, the compound containing an alpha-aminocarboxylic acid fragment can be selected from:

a) a compound wherein the N atom possesses a low basicity by substitution of the N atom with electron withdrawing groups or groups that are able to partly delocalise the N-lone pair; by low basicity the present invention understands an alpha-aminoalkylene carboxylic acid wherein the amino group is characterized by a pKb of about 3.0 or more, preferably by a pKb of 3.3 or more.

b) a polyamine wherein at least two N atoms are present and each N atom is separated by at least two carbon atoms from the next neighbouring N atom;

c) a compound wherein the N atom is substituted by alkyl groups.

Most preferred are:

a) nitrilotriacetic acid, ethylenediaminetetraacetic acid, diethylenetriaminepentaacetic acid, N-benzyliminodiacetic acid, N-methyliminodiacetic acid, iminodiacetic acid, N,N-bis(carboxymethyl)-1-glutamic acid, trisodium-N,N-bis (carboxymethyl)-alanine, N-cyanomethyl alanine, N,N-bis (cyanomethyl)-glycine, 4-morpholinoacetic acid, pyroglutamic acid, N-acetyl glycine, N,N-bis(carboxymethyl)-6-aminohexanoic acid, N-phenyl glycine, N-tosyl glycine, trans-1,2-cyclohexyldiaminotetraacetic acid monohydrate, N-phosphonomethyliminodiactic acid, iminodiacetic acid grafted on resin such as for example acidified Amberlite IRC748i;

b) 1,4,7,10-tetraazadodecane-1,4,7,10-tetraacetic acid, trans-1,2-cyclohexyldiaminotetracetic acid monohydrate;

c) N,N'-dimethylglycine.

In the method of the invention, individual species of alpha-aminoalkylenecarboxylic acids of interest may include, N,N-dimethylglycine, N-phthaloglycine, N-phenyl glycine, N-tosyl glycine, N-cyanomethyl glycine, N,N-bis-cyanomethyl glycine, 4-morpholineacetic acid, pyroglutamic acid, N-acetylglycine, N,N-bis(carboxymethyl)-6-aminohexanoic acid, N,N-bis(carboxymethyl)-1-glutamic acid, N-cyanomethyl alanine, trisodium N,N-bis(carboxymethyl)-alanine, iminodiacetic acid, N-methyl-iminodiacetic acid, N-benzyl iminodiacetic acid nitrilotriacetic acid, ethylene diamino tetraacetic acid, diethylenetriaminepentaacetic acid, N,N-bis(carboxymethyl)glycine, monocarboxymethylsarcosine and resins and polymers comprising at least one alpha-aminoalkylene carboxylic acid moiety, among others.

The use of neutralized or partially neutralized compounds containing an alpha-amino-carboxylic acid fragment requires an additional adjuvant with a lower pKa than the corresponding value of the alpha-aminocarboxylic acid group, which is added at the outset of the reaction in an amount at least sufficient to convert all the neutralized or partially neutralized carboxylic acid functions into the corresponding free carboxylic acid functions The acid catalyst used within the scope of the present invention is preferably a homogeneous Brønsted acid catalyst, optionally in the presence of a solvent, or a heterogeneous Brønsted acid catalyst, in the presence of a solvent, or a Lewis acid catalyst, in the presence of a solvent or a solvent being a Brønsted catalyst.

The homogeneous Brønsted acid catalyst preferably is selected from the group consisting of methanesulfonic acid, fluoromethanesulfonic acid, trichloromethanesulfonic acid, trifluoromethanesulfonic acid, acetic acid, trifluoroacetic acid, tert-butyl-sulfonic acid, p-toluenesulfonic acid, naphthalene sulfonic acid, 2,4,6-trimethylbenzene-sulfonic acid, perfluoro or perchloro sulfonic acids, perfluoro or perchloro carboxylic acids, hydrochloric acid, hydrobromic acid, hydroiodic acid, phosphorous acid, phosphoric acid and mixtures thereof.

In a particular embodiment of the present invention the Brønsted acid catalyst acts as catalyst and as solvent.

The heterogeneous Brønsted acid catalyst is preferably selected from the group of:

(i) solid acidic metal oxide combinations as such or supported onto a carrier material;

(ii) cation exchange resins selected from the group comprising copolymers of styrene, ethylvinyl benzene and divinyl benzene, functionalized so as to graft $SO_3H$ moieties onto the aromatic group and perfluorinated resins carrying carboxylic and/or sulfonic acid groups;

(iii) organic sulfonic, carboxylic and phosphonic Brønsted acids (which are substantially immiscible in the reaction medium at the reaction temperature);

(iv) an acid catalyst derived from:
the interaction of a solid support having a lone pair of electrons onto which is deposited an organic Brønsted acid; or
the interaction of a solid support having a lone pair of electrons onto which is deposited a compound having a Lewis acid site; or
heterogeneous solids functionalized by chemical grafting with a Brønsted acid group or a precursor therefore; and (v) heterogeneous heteropolyacids of the general formula $H_xPM_yO_z$ wherein P is selected from phosphorus and silicon and M is selected from tungsten and molybdenum and combinations thereof.

The heterogeneous Brønsted catalyst for use in the method of the present invention is preferably selected from the group consisting of macroreticular polymeric resins, representing a continuous open pore structure and comprising sulfonic, carboxylic and/or phosphonic acid moieties.

The heterogeneous Brønsted acid catalyst is substantially insoluble or immiscible in the reaction medium. The catalyst can form, at the reaction conditions, in particular the reaction temperature, a second liquid phase and can be recovered at the end of the reaction by conventional techniques such as filtration or phase separation.

Homogeneous Brønsted acid catalysts can leave a residue within the final reaction product. Nevertheless, there are known techniques for recovering the acid catalyst from the reaction medium such as ion exchange, nano filtration or electrodialysis which can be used to solve or mitigate the problems. Alternatively the end product can be separated e.g. by precipitation using a co-solvent and the Brønsted catalyst recovered and recycled after removal of the co-solvent.

The Lewis acid for being included in the solvent in general is a homogeneous or heterogeneous Lewis acid.

Brønsted acidic solvents can be replaced by Lewis acids dissolved or suspended in an organic solvent.

Preferred homogeneous Lewis acids can be selected from metal salts having the general formula:

$$MX_n$$

wherein M represents a main group element or transition metal like Li, B, Mg, Al, Bi, Fe, Zn, La, Sc, Yb, or Pd; X in $MX_n$ is typically an anion of an acid or acid derivative like Cl, OTf or $NTf_2$, where Tf stands for $CF_3SO_2$ and n is equal to the oxidation state of M, which can be from 1 to 5. Possible combinations are e.g. $LiNTf_2$, $Mg(OTf)_2$, $MgCl_2$, $ZnCl_2$, $PdCl_2$, $Fe(OTf)_3$, $Al(OTf)_3$, $AlCl_3$, $Bi(OTf)_3$, $BiCl_3$, $Sc(OTf)_3$, $Ln(OTf)_3$, $Yb(OTf)_3$. Preferably, combinations of a hard metal or a metal on the borderline between hard and soft according to the HSAB (hard soft acid base) concept like Li, Mg, Al, Sc, Zn, Bi, and weakly coordinating anions like OTf or $NTf_2$ are used. Examples of such preferred combinations are: $LiNTf_2$, $Mg(OTf)_2$, $Al(OTf)_3$, $Bi(OTf)_3$.

Preferred heterogeneous Lewis acids can be represented by species of discretionary selected subclasses created by interaction/bonding of homogeneous Lewis acids e.g. metal complexes, metal salts or organometallic species with polymeric organic or inorganic backbones. An example of such subclass is a polystyrene matrix with bonded $Sc(OTf)_2$ groups. Such catalyst can be prepared e.g. by interaction of a polystyrene sulfonic acid resin e.g. Amberlyst 15 with $Sc(OTf)_3$. The number of equivalents of Lewis acid functions can be determined in this case by different ways e.g. by acid base determination of the unreacted sulfonic acid groups, by quantitative determination of the liberated triflic acid and by ICP measurement of the amount of Sc on the resin.

Typical examples of suitable organic solvents are anisole; chlorinated and fluorinated hydrocarbons such as chlorobenzene, fluorobenzene, tetrachloroethane, tetrachloroethylene, dichloroethane, dichloromethane; polar solvents like diglyme, glyme, diphenyloxide, polyalkylene glycol derivatives with capped OH groups such as OR* where R* is a low alkyl or acyl group; aliphatic hydrocarbons such as hexane, heptane, cyclohexane; non-cyclic ethers like dibutyl ether, diethyl ether, diisopropyl ether, dipentylether, and butylmethylether; cyclic ethers like tetrahydrofuran, dioxane, and tetrahydropyran; mixed cyclic/non-cyclic ethers like cyclopentylmethylether; cyclic and non-cyclic sulfones like sulfolane; aromatic solvents like toluene, benzene, xylene; organic acetates like ethylacetate; organic nitriles like acetonitrile, benzonitrile; silicon fluids like polymethylphenyl siloxane or mixtures thereof non reactive ionic liquids like 1-n-butyl-imidazolium trifluoromethanesulfonate and 1-ethyl-3-methyl-imidazolium bis(trifluoromethyl sulfonyl)imide; or a mixture thereof.

The method of the present invention is started by mixing the alpha-aminoalkylenecarboxylic acid, the optional diluents and the acid catalyst. Optionally the alpha-aminoalkylenecarboxylic acid or the mixture of the alpha-aminoalkylene carboxylic acid and the optional diluents is cooled down to a temperature below ambient temperature, preferably to a temperature below about 10° C. before the addition of the acid catalyst, preferably the Brønsted acid catalyst.

The method of the invention comprises the step of forming a reaction mixture by gradually mixing the P—O—P anhydride moiety comprising compound, having one P-atom at the oxidation state (+III) and the other P-atom at the oxidation state (+III) or (+V), preferably tetraphosphorus hexaoxide, and the mixture comprising the aminoalkanecarboxylic acid, the acid catalyst, preferably a Brønsted acid catalyst, or a solvent being a Brønsted catalyst, and optionally the diluent, standing at an adequate temperature (preferably comprised between about 20° C. and about 120° C.) and maintaining this reaction mixture at an adequate temperature (preferably at a temperature comprised between about 20° C. and about 100° C.), during an adequate period, preferably for at least about 10 minutes after the completion of the mixing process.

In particular embodiment of the present invention, the method comprises the step of forming a reaction mixture by gradually adding the P—O—P anhydride moiety comprising compound, having one P-atom at the oxidation state (+III) and the other P-atom at the oxidation state (+III) or (+V), preferably tetraphosphorus hexaoxide, to the mixture comprising the aminoalkanecarboxylic acid, the acid catalyst, preferably a Brønsted acid catalyst or a solvent being a Brønsted catalyst, and optionally the diluent, standing at an adequate temperature (preferably comprised between about 20° C. and about 120° C.) and maintaining this reaction mixture at an adequate temperature (preferably at a temperature comprised between about 20° C. and about 100° C.), during an adequate period, preferably for at least about 10 minutes after the completion of the mixing process.

In another embodiment of the present invention, the method comprises the step of forming a reaction mixture by gradually adding the mixture comprising the aminoalkanecarboxylic acid, the acid catalyst, preferably a Brønsted acid catalyst or a solvent being a Brønsted catalyst, and optionally the diluent, standing at an adequate temperature (preferably comprised between about 20° C. and about 120° C.) to the P—O—P anhydride moiety comprising compound, having one P-atom at the oxidation state (+III) and the other P-atom at the oxidation state (+III) or (+V), preferably tetraphosphorus hexaoxide, and maintaining this reaction mixture at an adequate temperature (preferably at a temperature comprised between about 20° C. and about 100° C.), during an adequate period, preferably for at least about 10 minutes after the completion of the mixing process.

The ratio of the moles of acid catalyst to the alpha-aminoalkylene carboxylic acid equivalents is comprised between about 0.01 and about 11.0, preferably between about 0.1 and about 9.0, more preferably between about 1.0 and about 7.0 and most preferably between about 2 and about 5.

According to the invention, the mixture of alpha-aminoalkylene carboxylic acid and acid catalyst, optionally comprising the diluent(s), is thereafter brought to a temperature comprised between about 20° C. and about 120° C. and preferably between about 20° C. and about 80° C.

To the mixture standing at a temperature comprised between about 20° C. and about 120° C. and preferably between about 20° C. and about 80° C., the P—O—P anhydride moiety comprising compound is slowly added, under stirring, in such a way that the temperature of the reaction mixture does not exceed a pre-fixed maximal temperature set-point.

In the method of the invention, the equivalent ratio of alpha-aminoalkylenecarboxylic acid to P—O—P anhydride moiety is comprised between about 0.2 and about 4.5, preferably between about 0.3 and about 3.0 and more preferably between about 0.5 and about 1.5.

The ratio of the alpha-aminoalkylene carboxylic acid equivalents to the moles of tetraphosphorus hexaoxide is comprised between about 1.0 and about 12.0, preferably between about 1.5 and about 8.0 and more preferably between about 2.0 and about 6.0.

After completion of the mixing process of the P—O—P anhydride moiety comprising compound and the alpha-aminoalkylenecarboxylic acid, the reaction mixture is kept at the temperature of the mixing process or is heated up or cooled down to a temperature comprised between about 20° C. and about 100° C., preferably between about 40° C. and about 90° C. and more preferably between about 50° C. and about 80° C. and maintained at that temperature for a period of time comprised between about 10 minutes and about 72 hours, preferably between about 30 minutes and about 48 hours, more preferably between about 1 hour and about 24 hours and most preferably between about 2 hours and about 10 hours in order to favour the conversion of alpha-aminoalkylenecarboxylic acid into alpha-aminoalkylenephosphonic acid (i.e. the replacement of a carboxylic acid group by a phosphonic acid group).

During the reaction of the P—O—P anhydride moiety comprising compound with alpha-aminoalkylenecarboxylic acid, carbon monoxide and the P—C moiety are formed in equimolar amounts. During the conversion of the compound containing an alpha-aminocarboxylic acid fragment, one equivalent of CO will be formed for each converted equivalent of alpha-amino carboxylic acid fragment. CO will leave the reaction mixture as a gas of very high purity. This CO gas can be used in many applications like e.g. as a fuel, in combination with hydrogen for methanol and Fischer-Tropsch hydrocarbons manufacture, for hydroformylation reactions, for alcohol carbonylation e.g. carbonylation of methanol to acetic acid or the conversion of methylacetate to acetic anhydride.

After completion of the conversion of alpha-aminoalkylenecarboxylic acid into alpha-aminoalkylenephosphonic acid, its dehydrated forms or their phosphonate esters, water is optionally added to the reaction mixture in order to convert the dehydrated forms of alpha-aminoalkylenephosphonic acid or their phosphonate esters into alpha-aminoalkylenephosphonic acid or its phosphonate esters and to hydrolyse the unreacted P—O—P anhydride moieties, if present.

Preferably, water is added to the reaction mixture after it is cooled down to room temperature. Alternatively the reaction mixture can be cooled down through the addition of the water. This hydrolysis is performed at a temperature comprised between room temperature and about 100° C. for a period comprised between about 10 minutes and about 48 hours and preferably between about 1 hour and about 24 hours.

Unreacted P—O—P anhydride moieties may be the result of an incomplete conversion or of a non-stoichiometric amount of P—O—P anhydride group comprising compounds, forming the reaction mixture.

For the case of a substantial complete conversion and a stoichiometric loading of the reactants, the addition of water and thus the hydrolysis step can be omitted.

The yield of the conversion of alpha-aminoalkylenecarboxylic acid into alpha-aminoalkylenephosphonic acid, according to the method of the present invention, is preferably at least about 50% advantageously at least about 80% even more advantageously at least about 95%.

EXAMPLES

The present invention will be described in detail in the following examples that illustrate the invention. They are merely meant to exemplify the present invention, but are not destined to limit the scope of the present invention.

Example 1

In a round bottom flask equipped with a mechanical stirrer, a thermometer and a condenser, 7.26 g (60 mmole) of 4-morpholinoacetic acid was mixed with 22 ml (249 mmole) of trifluoromethanesulfonic acid. To the mixture, standing at room temperature, 5.50 g (25 mmole) of tetraphosphorus hexaoxide was slowly added while stirring. After the completion of the tetraphosphorus hexaoxide addition, the reaction mixture was heated to 70° C. and stirred for 7 hours at 70° C. During the addition of the tetraphosphorus hexaoxide and the subsequent 7 hour reaction period, the formation of carbon monoxide was observed. Then 20 ml of water was added to the reaction mixture. The solution thus obtained was analyzed by $^1$H-NMR and $^{31}$P-NMR spectroscopy. 94.7% weight of 4-morpholinomethylphosphonic acid was detected.

Example 2

In a round bottom flask equipped with a mechanical stirrer, a thermometer and a condenser, 15.7 g (82 mmole) nitrilo triacetic acid was mixed with 49.8 ml (767 mmole) of methanesulfonic acid. The mixture was heated to 75° C. and 13.4 g (61 mmole) tetraphosphorus hexaoxide was slowly added while stirring. After the completion of the tetraphosphorus hexaoxide addition, the reaction mixture was stirred for 30 minutes at 75° C. During the addition of the tetraphosphorus hexaoxide and the subsequent 30 minutes reaction period, the formation of carbon monoxide was observed. Then 20 ml of water was added to the reaction mixture. The solution thus obtained was analyzed by $^{31}$P-NMR spectroscopy. 95.6% weight of aminotrismethylenephosphonic acid was detected.

Example 3

In a round bottom flask equipped with a mechanical stirrer, a thermometer and a condenser, 10.00 g (65.4 mmole) N,N-biscyanomethyl glycine was mixed with 50 ml acetonitrile and 12.7 ml (196 mmole) of methanesulfonic acid. To the mixture, standing at room temperature, 3.60 g (16.3 mmole) of tetraphosphorus hexaoxide was slowly added while stirring. After the completion of the tetraphosphorus hexaoxide addition the reaction mixture was stirred for 5 hours at 40° C. and subsequently for 16 hours at ambient temperature. The acetonitrile then was distilled off and the residue was dissolved in 50 ml of water. The solution comprising the residue and the water was heated to 90° C. and stirred for 7 hours at 90° C. The solution thus obtained was cooled down to ambient temperature upon which 12.67 g of precipitate was formed. The precipitate was isolated through filtration. Solid and filtrate were analyzed by $^1$H-NMR and $^{31}$P-NMR spectroscopy. The solid was composed of 97.3% weight N,N-phosphonomethyliminodiacetic acid.

Example 4

Amberlite IRC 748 is a cation exchange resin consisting of a macroporous styrene divinylbenzene matrix with grafted iminodiacetic acid moieties.

In a column 23.4 g Amberlite IRC 748i (as the Na$^+$ form) was placed and a 0.1 M aqueous HCl solution was passed slowly through the column. The pH of the filtrate was checked several times until a pH of 2 was observed (after approx. 200 ml). The column was emptied and the beads were washed with 100 ml 1,4-dioxane and 200 ml diethylether. Then the beads were dried in an oven for 4 hours at 50° C. and in a desiccator over P$_2$O$_5$ overnight.

In a round-bottom flask equipped with a mechanical stirrer, a thermometer and a condenser, 2.00 g (21.6 mmole COOH functions) of the proton form of the acidified Amberlite IRC748i (as prepared hereabove) was mixed with 5.6 ml methanesulfonic acid. Subsequently, the reaction mixture was heated to 85° C. and 1.19 g (5.4 mmole) P$_4$O$_6$ was added. The reaction mixture was stirred for 6 hours at 85° C. During the addition and the reaction time the evolution of CO was observed. The reaction mixture was cooled afterwards to 25° C. and slowly 30 ml H$_2$O was added. The beads were filtered off and washed twice with 100 ml H$_2$O and kept in a desiccator over P$_2$O$_5$ for overnight. The beads were analysed by FTIR-spectroscopy. The bands corresponding to COOH functions had completely disappeared while new bands had appeared in the regions typical for the stretching of P=O groups of phosphonates.

In table 1 a series of examples, according to the present invention, are reported.

In this table:

Column 1: indicates the identification number of the example.

Column 2: indicates the type of alpha-aminoalkylenecarboxylic acid put into reaction with tetraphosphorus hexaoxide.

Column 3: indicates the number of mmoles of alpha-aminoalkylenecarboxylic acid with into brackets the number of carboxylic acid milliequivalents.

Column 4: indicates the type of catalyst.

Column 5: indicates the number of mmoles of catalyst.

Column 6: indicates the number of mmoles of tetraphosphorus hexaoxide or of reactive 'P(+III)' atoms.

Column 7: indicates the ratio of mmoles of alpha-aminoalkylenecarboxylic acid to mmoles of tetraphosphorus hexaoxide or of reactive 'P(+III)' atoms with into brackets the ratio of carboxylic acid milliequivalents of the α-aminoalkylenecarboxylic acid to mmoles of tetraphosphorus hexaoxide or of reactive 'P(+III)' atoms.

Column 8: indicates the ratio of mmoles of catalyst to mmoles of alpha-aminoalkylene carboxylic acid with into brackets the ratio of mmoles of catalyst to carboxylic acid milliequivalents of the alpha-aminoalkylenecarboxylic acid.

Column 9: indicates the ratio of mmoles catalyst to mmoles of tetraphosphorus hexaoxide or reactive 'P(+III)' atoms.

Column 10: indicates the temperature (° C.) of the mixture comprising the α-aminoalkylenecarboxylic acid and catalyst to which the tetraphosphorus hexaoxide or the reactive 'P(+III)' atoms is added; this temperature is maintained during the whole tetraphosphorus hexaoxide or reactive 'P(+III)' atoms addition.

Column 11: indicates the temperature (° C.) and time (hrs) conditions of the reaction mixture upon completion of the tetraphosphorus hexaoxide or reactive 'P(+III)' atoms addition.

Column 12: indicates the temperature (° C.) and time (hrs) conditions of the reaction mixture comprising water, for hydrolysis of the dehydrated forms of α-aminoalkylenephosphonic acid or their phosphonate esters and of unreacted tetraphosphorus hexaoxide or reactive 'P(+III)' atoms Column 13: indicates the reaction yield, in % by weight, as measured by $^1$H-NMR and $^{31}$P-NMR spectroscopy.

The alpha-aminoalkylenephosphonic acids prepared in the examples of table 1 are:

Example 5

(N,N-dimethylamino)methylphosphonic acid

Example 6 and 7

4-morpholinomethylphosphonic acid

Example 8 to 10

N,N-bis(phosphonomethyl)-6-amino-hexanoic acid

Example 11 phthalimidomethylphosphonic acid

Example 12

N-phenyl-aminomethylphosphonic acid

Example 36

N-tosyl-aminomethylphosphonic acid

Example 14 aminomethylphosphonic acid

Example 15 to 18

5-phosphono-2-pyrrolidone and 4-amino-4-phosphonobutyric acid

Example 19 ethylenediamine-tetramethylenephosphonic acid

Example 20 diethylenetriaminopentamethylenephosphonic acid

Example 21 to 26

N,N-bis(phosphonomethyl)-4-amino-4-phosphono-butyric acid

Example 27

N-benzyliminobismethylenephosphonic acid

Example 28 to 33

N,N-bis(phosphonomethyl)-1-amino-ethyl-phosphonic acid

Example 34 to 36 imino (bismethylenephosphonic acid)

Example 37

N-methyl-imino (bismethylenephosphonic acid)

Example 38 to 41

N-phosphonomethyl glycine

Example 42 to 46 phosphonomethyliminodiacetic acid

Example 47 to 58 and 63 and 65 to 67 aminotrismethylenephosphonic acid.

Example 59

N-phosphonomethylglycine

Example 60 iminodiphosphonic acid grafted groups on a macroporous styrene divinylbenzene matrix.

Example 61 trans-1,2-cyclohexyldiaminotetramethylenephosphonic acid

Example 62

1,4,7,10-tetraazadodecane-1,4,7,10-tetramethylenephosphonic acid

Example 64

N-methyl-iminodiphosphonic acid.

TABLE 1

| Ex | Aminoalkylene COOH | COOH (mmole) | Catalyst | Cata (mmole) | $P_4O_6$ (mmole) | COOH $P_4O_6$ | Cata COOH | Cata $P_4O_6$ | $T_1$ °C. | $T_2$/time °C./hrs | $T_3$/time °C./hrs | Yield % w |
|---|---|---|---|---|---|---|---|---|---|---|---|---|
| 5 | N,N-dimethyl glycine | 9.7 | Trifluoromethane sulfonic acid | 45 | 4.8 | 2.0 | 4.6 | 18.75 | 55/4 | 80/24 | 25 | 4.1 |
| 6 | Morpholineacetic acid | 50 | Trifluoromethane sulfonic acid | 248.6 | 12.5 | 5.0 | 5.0 | 19.9 | 25 | 80/6 | 25 | 98.1 |
| 7 | Morpholineacetic acid | 50 | Trifluoromethane sulfonic acid | 248.6 | 25 | 2.0 | 5.0 | 10.0 | 25 | 70/6 | 25 | 94.7 |
| 8 | N,N-bis(carboxy methyl)-6-amino hexanoic acid | 4.3 (8.6) | Methanesulfonic acid | 77 | 2.2 | 2.0 (3.9) | 17.9 | 35 (9.0) | 60 | 60/24 | 25 | 52.3 |
| 9 | N,N-bis(carboxy methyl)-6-amino hexanoic acid | 4.3 (8.6) | Methanesulfonic acid | 77 | 4.3 | 1.0 (2.0) | 17.9 | 17.9 (9.0) | 60 | 100/16 | 25 | 48.7 |
| 10 | N,N-bis(carboxy methyl)-6-amino hexanoic acid | 4.3 (8.6) | Methanesulfonic acid | 77 | 3.6 | 1.2 (2.4) | 17.9 | 21.4 (9.0) | 80 | 80/6 | 25 | 64.5 |
| 11 | N-Phtaloglycine | 40 | Trifluoromethane sulfonic acid | 56.5 | 10 | 4.0 | 1.4 | 5.7 | 70 | 70/3 | 25 | 98.6 |
| 12 | N-Phenyl glycine | 40.0 | Trifluoromethane sulfonic acid (dioxane, 5 ml) | 113.0 | 10.0 | 2.8 | 0.8 | 11.3 | 25 | 50/7 | 25 | 42.1 |
| 13 | N-Tosyl glycine | 4.4 | Methanesulfonic acid | 46.2 | 1.1 | 4.0 | 10.5 | 42.0 | 25 | 50/3 | 25 | 51.2 |
| 14 | N-acetylglycine | 40 | Methanesulfonic acid | 153 | 10 | 4.0 | 3.8 | 15.3 | 80 | 100/3 | 100/1 | 6.0 (1*) |
| 15 | Pyroglutamic acid | 400 | Methanesulfonic acid | 1385.9 | 100 | 4.0 | 3.5 | 13.9 | 25 | 70/12 | 25 | 87.8 (2*) |
| 16 | Pyroglutamic acid | 30.0 | Methanesulfonic acid | 308.0 | 7.5 | 4.0 | 10.3 | 41.1 | 60 | 60/16 | 60/2 | 58.1 (3*) |
| 17 | Pyroglutamic acid | 20.0 | Trifluoromethane sulphhonic acid | 169.5 | 5.0 | 4.0 | 8.5 | 33.9 | 60 | 60/16 | 60/2 | 72.1 (4*) |
| 18 | Pyroglutamic acid | 30.0 | Trifluoroacetic acid | 300.4 | 7.5 | 4.0 | 10.0 | 40.0 | 60 | 60/16 | 60/2 | 17.9 (5*) |
| 19 | Ethylenediamine tetraacetic acid | 61.4 (245.6) | Methanesulfonic acid | 1539.9 | 61.6 | 1.0 (4.0) | 25.1 | 25.0 (6.3) | 45 | 70/1 80/1 | 25 | 94.5 |
| 20 | Diethylenetriamine pentaacetic acid | 49.1 (245.5) | Methanesulfonic acid | 1385.9 | 61.6 | 0.8 (4.0) | 28.2 | 22.5 (5.6) | 55 | 80/1 90/1 | 25 | 89.6 |
| 21 | N,N-bis(carboxy methyl)-1-glutamic acid | 3.8 (11.4) | Trifluoroacetic acid | 60 | 2.8 | 1.4 (4.1) | 15.8 | 21.4 (5.3) | 50 | 50/2 65/72 | 25 | 71.1 |
| 22 | N,N-bis(carboxy methyl)-1-glutamic acid | 3.8 (11.4) | Methanesulfonic acid | 60.1 | 2.8 | 1.4 (4.1) | 15.8 | 21.4 (5.3) | 50 | 50/2 80/0.25 | 25 | 52.5 |
| 23 | N,N-bis(carboxy methyl)-1-glutamic acid | 7.6 (22.8) | Trifluoromethanesulfonic acid | 90.4 | 5.6 | 1.4 (4.1) | 11.9 | 16.1 (4.0) | 50 | 50/3 | 25 | 9.0 |
| 24 | N,N-bis(carboxy methyl)-1-glutamic acid | 7.6 (22.8) | Trifluoroacetic acid | 93.9 | 5.6 | 1.4 (4.1) | 12.4 | 16.8 (4.1) | 45 | 45/3 60/1 | 25 | 39.5 |
| 25 | N,N-bis(carboxy methyl)-1-glutamic acid | 7.6 (22.8) | Methanesulfonic acid | 107.8 | 5.6 | 1.4 (4.1) | 14.2 | 19.3 (4.7) | 45 | 45/2 60/1 | 25 | 18.5 (6*) |
| 26 | N,N-bis(carboxy methyl)-1-glutamic acid | 7.6 (22.8) | Methanesulfonic acid | 107.8 | 5.6 | 1.4 (4.1) | 14.2 | 19.3 (4.7) | 45 | 50/2 60/1 | 25 | 46.7 (7*) |
| 27 | N-Benzylimino diacetic acid | 10.8 (21.6) | Trifluoromethanesulfonic acid (MeCN, 70 ml) | 10.8 | 5.4 | 2.0 (4.0) | 1.0 | 2.0 (0.5) | 25 | 75/3 | 25 | 81.2 |
| 28 | Trisodium N,N-bis(carboxy methyl)-alanine | 5.1 (15.3) | Methanesulfonic acid | 138.6 | 2.6 | 2.0 (5.9) | 27.2 | 53.3 (9.1) | 25 | 35/16 | 25 | 55.6 |
| 29 | Trisodium N,N-bis(carboxy methyl)-alanine | 11.9 (35.7) | Methanesulfonic acid | 231 | 6.0 | 2.0 (6.0) | 19.4 | 38.5 (6.5) | 55 | 60/16 | 25 | 32.0 |
| 30 | Trisodium N,N-bis(carboxy methyl)-alanine | 11.9 (35.7) | Methanesulfonic acid | 123.2 | 3.0 | 4.0 (11.9) | 10.4 | 41.1 (3.5) | 55 | 65/4 | 25 | 6.8 |
| 31 | Trisodium N,N-bis(carboxy methyl)-alanine | 10.2 (30.6) | Methanesulfonic acid | 277.2 | 7.6 | 1.3 (4.0) | 27.2 | 36.5 (9.1) | 50 | 55/4 | 25 | 51.9 |
| 32 | Trisodium N,N-bis(carboxy methyl)-alanine | 10.2 (30.6) | Methanesulfonic acid | 277.2 | 2.6 | 3.9 (11.8) | 27.2 | 106.6 (9.1) | 50 | 55/4 | 25 | 16.4 |
| 33 | Trisodium N,N-bis(carboxy methyl)-alanine | 5.1 (15.3) | Methanesulfonic acid | 138.6 | 1.3 | 3.9 (11.8) | 27.2 | 106.6 (9.1) | 30 | 35/16 | 25 | 50.1 |
| 34 | Iminodiacetic acid | 7.5 (15.0) | Trifluoromethane sulfonic acid | 59.9 | 3.8 | 2.0 (3.9) | 8.0 | 15.8 (4.0) | 80 | 80/4 | 25 | 97.8 |

TABLE 1-continued

| Ex | Aminoalkylene COOH | COOH (mmole) | Catalyst | Cata (mmole) | 'P(+III)' (mmole) | COOH 'P(+III)' | Cata COOH | Cata 'P(+III)' | T₁ °C. | T₂/time °C./hrs | T₃/time °C./hrs | Yield % w |
|---|---|---|---|---|---|---|---|---|---|---|---|---|
| 35 | Iminodiacetic acid | 15.0 (30.0) | Lithium (bistri- fluoromethyl sulphonyl) imide | 1.5 | 7.5 | 2.0 (4.0) | 0.1 (0.05) | 0.2 | 75 | 75/24 | 75/5 | 5.9 |
| 36 | Iminodiacetic acid | 46.6 (93.2) | Nafion SAC-13 | 11.6 | 23.3 | 2.0 (4.0) | 0.3 (0.1) | 0.5 | 55 | 55/16 | 55/5 | 1.9 |
| 37 | methylimino diacetic acid | 123.0 (246.) | Methanesulfonic acid | 766.9 | 61.4 | 2.0 4.0 | 6.2 (3.1) | 12.5 | 65 | 95/8 | 25 | 86.6 |
| 38 | N-cyanomethyl glycine | 35.2 | Trifluoromethane sulfonic acid | 88.1 | 8.8 | 4.0 | 2.5 | 10.0 | 25 | 65/5 | 80/7 | 8.3 |
| 39 | N-cyanomethyl glycine | 35.2 | Trifluoroacetic acid Trifluoromethanesulfonic acid | 134.2 88.1 | 8.8 | 4.0 | 6.3 | 25.3 | 25 | 40/16 | 100/7 | 47.6 |
| 40 | N-cyanomethyl glycine | 35.2 | Trifluoromethane sulfonic acid | 88.1 | 8.8 | 4.0 | 6.3 | 25.3 | 25 | 60/2 | 90/7 | 9.2 |
| 41 | N-cyanomethyl glycine | 20.0 | Trifluoromethanesulfonic acid | 56.5 | 5.0 | 4.0 | 2.8 | 11.3 | 25 | 50/4 | 25 | 62.5 |
| 42 | N,N-biscyano methyl glycine | 65.4 | Methanesulfonic acid | 246.4 | 16.3 | 4.0 | 3.8 | 15.1 | 40 | 70/5 | 25 | 39.3 |
| 43 | N,N-biscyano methyl glycine | 65.4 | Methanesulfonic acid | 130.9 | 16.3 | 4.0 | 2.0 | 8.0 | 25 | 30/2 | 25 | 37.6 (8*) |
| 44 | N,N-biscyano methyl glycine | 65.4 | Trifluoromethane sulfonic acid | 130.0 | 16.3 | 4.0 | 2.0 | 8.0 | 25 | 30/4 | 100/7 | 86.1 (9*) |
| 45 | N,N-bis(cyano methyl)-glycine | 20.0 | Trifluoromethane sulfonic acid (MeCN, 10 ml) | 10.0 | 5.0 | 4.0 | 0.5 | 2 | 30 | 30/3 | 25 | 65.3 (10*) |
| 46 | N,N-biscyano methyl glycine | 65.4 | Methanesulfonic acid | 195.6 | 16.3 | 4.0 | 3.0 | 12.0 | 25 | 40/5 25/16 | 90/7 | 97.3 (11*) |
| 47 | Nitrilotriacetic acid | 10.0 (30) | Methanesulfonic acid | 92.4 | 7.6 | 1.3 (3.9) | 9.2 (3.1) | 12.2 | 55 | 55/2 75/1 | 25 | 24.2 |
| 48 | Nitrilotriacetic acid | 10.5 (31.5) | Trifluoroacetic acid | 127.2 | 7.7 | 1.4 (4.1) | 12.1 (4.0) | 16.5 | 45 | 50/3 | 25 | 8.5 (12*) |
| 49 | Nitrilotriacetic acid | 10.5 (31.5) | Trifluoromethanesulfonic acid | 122.0 | 7.7 | 1.4 (4.1) | 11.6 (3.9) | 15.8 | 50 | 50/1 | 25 | 72.5 |
| 50 | Nitrilotriacetic acid | 10.5 (31.5) | Trifluoromethanesulfonic acid | 7.7 | 7.7 | 1.4 (4.1) | 0.7 (0.2) | 1.0 | 50 | 55/4 | 65/1 | 82.2 (13*) |
| 51 | Nitrilotriacetic acid | 10.5 (31.5) | Trifluoromethanesulfonic acid | 7.7 | 7.7 | 1.4 (4.1) | 0.7 (0.2) | 1.0 | 55 | 55/2 65/2 | | 85.5 |
| 52 | Nitrilotriacetic acid | 10.5 (31.5) | Trifluoromethanesulfonic acid | 2.9 | 7.7 | 1.4 (4.1) | 0.28 (0.09) | 0.4 | 50 | 60/24 | 25 | 52.8 |
| 53 | Nitrilotriacetic acid | 31.5 (94.5) | Trifluoroacetic acid | 382.4 | 23.3 | 1.4 (4.1) | 12.1 (4.0) | 16.4 | 55 | 55/3 60/1 | 55/2 | 89.4 |
| 54 | Nitrilotriacetic acid | 31.5 (94.5) | Nafion SAC-13 | 1.16 | 23.3 | 1.4 (4.1) | 0.04 (0.01) | 0.05 | 55 | 55/24 | 25 | 34.9 (14*) |
| 55 | Nitrilotriacetic acid | 131 (393) | Methanesulfonic acid | 1093.3 | 88.0 | 1.5 (4.5) | 8.3 (2.8) | 1.2 | 75 | 75/0.5 | | 97 |
| 56 | Nitrilotriacetic acid | 82 (246) | Methanesulfonic acid | 766.9 | 61.0 | 1.3 (4.0) | 9.4 (3.1) | 12.6 | 75 | 75/0.5 | | 98.8 |
| 57 | Nitrilotriacetic acid | 133 (399) | Phosphorous acid | 1000.0 | 88.0 | 1.5 (4.5) | 7.5 (2.5) | 11.4 | 80 | 95/8 | 25 | 69.6 |
| 58 | Nitrilotriacetic acid | 10.5 (31.5) | Magnesium triflate (MeCN, 20 ml) | 7.7 | 7.7 | 1.4 (4.1) | 1.4 (4.1) | 1 | 50 | 50/24 | 25 | 10.6 |
| 59 | N-cyanomethyl alanine | 23.4 | Trifluoromethane sulfonic acid | 58.8 | 5.9 | 4.0 | 2.5 | 10.0 | 25 | 50/6 | 100/9 | 60.0 |
| 60 | Acidified Amberlite IRC748i | 540 | Trifluoromethanesulfonic acid (MeCN, 350 ml) | 135.6 | 135.5 | 4.0 | 4.0 | 1 | 55 | 80/4 45/1 | 25 | (15*) |
| 61 | C₆H₁₀-1,2-(N(CH₂CO₂H)₂)₂*H₂O | 20.0 (80.0) | Methanesulfonic acid | 308.0 | 20.0 | 1.0 (1.0) | 15.4 (3.9) | 15.4 | 25 | 50/3 | 25 | 87.0 |
| 62 | 1,4,7,10-tetraazadodecane-1,4,7,10-tetraacetic acid | 2.5 (10.0) | Trifluoromethane sulfonic acid | 33.9 | 2.5 | 1.0 (4.0) | 13.7 (3.4) | 13.7 | 25 | 60/3 | 25 | 86.3 |
| 63 | PMIDA | 20.0 (40.0) | Methanesulfonic acid | 154.2 | 10.0 | 2.0 (4.0) | 7.7 (3.9) | 15.4 | 25 | 60/2 | 25 | 87.1 |
| 64 | N-methyl-iminodiacetic acid | 123.0 (246.0) | Methanesulfonic acid | 767.0 | 61.4 | 2.0 (4.0) | 6.2 (3.1) | 12.5 | 65 | 95/8 | 25 | 86.6 |
| 65 | Nitrilotriacetic acid | 20.0 (60.0) | Methanesulfonic acid | 231.0 | 30.0 | 0.7 (2.0) | 11.6 (3.9) | 7.7 | 25/1 | 50/3 | 25 | 92.7 (16*) |

TABLE 1-continued

| 66 | Nitrilotriacetic acid | 40.0 (120.0) | Methanesulfonic acid | 308.0 | 30.0 | 1.3 (4.0) | 7.7 2.6 | 10.3 | 60 | 60/3 | 25 | 70.0 (17*) |
|---|---|---|---|---|---|---|---|---|---|---|---|---|
| 67 | Nitrilotriacetic acid | 5.0 (15.0) | Methanesulfonic acid | 77.0 | 15.0 | 0.3 (1.0) | 15.4 5.1 | 5.1 | 25 | 30/2 | 25 | 93.4 (18*) |

(1*) The reaction mixture, after completion of the reaction of $P_4O_6$ and N-acetylglycine was cooled down to room temperature and the pH of the reaction mixture was increased to above 10. The reaction mixture was heated for 1 hr at 100° C.; 6% by weight of aminomethylphosphonic acid was formed through hydrolysis of acetamidomethylphosphonic acid.
(2*) Pyroglutamic acid is converted into 5-phosphono-2-pyrrolidone (yield: 87.8%). When further stirring the reaction mixture, comprising the water, for 12 hours at 100° C., the 5-phosphono-2-pyrrolidone is further hydrolyzed and a mixture comprising 11.7% by weight of 5-phosphono-2-pyrrolidone and 77.1% by weight of 4-amino-4-phosphonobutyric acid is obtained.
(3*) 55.7% by weight of 5-phosphono-2-pyrrolidone and 41.7% by weight of 4-amino-4-phosphonobutyric acid were formed.
(4*) 70.2% by weight of 5-phosphono-2-pyrrolidone and 25.9% by weight of 4-amino-4-phosphonobutyric acid were formed.
(5*) 17.7% by weight of 5-phosphono-2-pyrrolidone and 1.5% by weight of 4-amino-4-phosphonobutyric acid were formed.
(6*) 18.5% by weight of N,N-bis(phosphonomethyl)-4-amino-4-phosphono-butyric acid and 34.4% by weight of N,N-bis(phosphonomethyl)-4-amino-glutamic acid were formed.
(7*) 46.7% by weight of N,N-bis(phosphonomethyl)-4-amino-4-phosphono-butyric acid and 12.0% by weight of N,N-bis(phosphonomethyl)-4-amino-glutamic acid were formed.
(8*) 37.6% by weight of N,N-bis(cyanomethyl)aminomethyl phosphonic acid and 15.1% by weight of phosphonomethyliminodiacetic acid were formed.
(9*) After hydrolysis (stirring 7 hrs at 100° C.), the reactor content was cooled to ambient temperature whereupon a precipitate of phosphonomethyliminodiacetic acid is formed. After filtration the filtrate comprises 19.3% weight of phosphonomethyliminodiacetic acid. The solid is composed for 86.1% by weight of phosphonomethyliminodiacetic acid.
(10*) The obtained solution comprises 13.4% by weight of phosphonomethyliminodiacetic acid and 65.3% by weight of N-phosphonomethyliminodiacetonitrile.
(11*) *) After hydrolysis (stirring 7 hrs at 100° C.), the reactor content was cooled to ambient temperature whereupon a precipitate of phosphonomethyliminodiacetic acid is formed. After filtration the filtrate comprises 26.2% weight of phosphonomethyliminodiacetic acid. The solid is composed for 97.3% by weight of phosphonomethyliminodiacetic acid.
(12*) The obtained solution comprises 8.5% by weight of aminotrismethylenephosphonic acid and 9.5% by weight of aminotrismethylenephosphonic acid-N-oxide.
(13*) The obtained solution comprises 82.2% weight of aminotrismethylenephosphonic acid and 0.8% weight of aminotrismethylenephosphonic acid-N-oxide.
(14*) Nafion™ SAC-13: fluorosulfonic acid Nafion™ polymer on amorphous silica, 10-20% (porous nanocomposite). The obtained solution comprises comprises 34.9% weight of aminotrismethylenephosphonic acid and 2.4% weight of aminotrismethylenephosphonicacid-N-oxide.
(15*) Amberlite IRC 748 is an iminodiacetic acid chelating cation exchange resin based on a macroporous styrene divinylbenzene matrix. After reaction with $P_4O_6$, the reaction mixture was cooled down to room temperature and the solid was filtered and washed. FTIR spectroscopy indicated the bands corresponding to the —COOH groups had almost disappeared, meanwhile new bands, typical for phosphonate groups had appeared
Wherein the 'P(+III)' compound is obtained from combining in
(16*) Example 65: 60 mmole phosphorous acid and 30 mmole tetraphosphorus decaoxide,
(17*) Example 66: 120 mmole dimethylphosphite and 30 mmole tetraphosphorus decaoxide, and wherein in
(18*) Example 67 the P(III) comprising compound is tetraethylpyrophosphite.

The invention claimed is:

1. A method for the synthesis of an alpha-aminoalkylenephosphonic acid or an ester thereof, the method comprising the steps of:
    a) forming a reaction mixture by mixing an alpha-aminoalkylenecarboxylic acid, an acid catalyst, and a compound comprising one or more P—O—P anhydride moieties, wherein at least one of the P—O—P anhydride moieties comprises one P-atom at the oxidation state (+III) and the other P-atom at the oxidation state (+III) or (+V); and
    b) recovering the resulting alpha-aminoalkylenephosphonic acid or an ester thereof from said reaction mixture, wherein at least one carboxylic acid group in the alpha-aminoalkylenecarboxylic acid is replaced by a phosphonic acid group or an ester thereof, and wherein said alpha-aminoalkylenecarboxylic acid is selected from the group consisting of nitrilotriacetic acid, ethylenediaminetetraacetic acid, diethylenetriaminepentaacetic acid, N-benzyliminodiacetic acid, N-methyliminodiacetic acid, iminodiacetic acid, N,N-bis(carboxymethyl)-1-glutamic acid, trisodium-N,N-bis(carboxymethyl)-alanine, N-cyanomethyl alanine, N,N-bis(cyanomethyl)-glycine, 4-morpholinoacetic acid, pyroglutamic acid, N-acetyl glycine, N,N-bis(carboxymethyl)-6-aminohexanoic acid, N-phenyl glycine, N-tosyl glycine, trans-1,2-cyclohexyldiaminotetraacetic acid monohydrate, N-phosphonomethyliminodiacetic acid, iminodiacetic acid grafted on resin, 1,4,7,10-tetraazadodecane-1,4,7,10-tetraacetic acid, N-phthaloglycine, and N'N'-dimethylglycine; and
    said P—O—P anhydride moiety comprising compound is selected from the group consisting of tetraphosphorus hexaoxide, $P_4O_7$, $P_4O_8$, $P_4O_9$, tetraethylpyrophosphite, and combinations thereof.

2. The method according to claim 1 wherein the reaction mixture is formed by gradually adding the P—O—P anhydride moiety comprising compound to a mixture comprising the alpha-aminoalkylenecarboxylic acid and the acid catalyst.

3. The method according to claim 1 wherein the reaction mixture is formed by gradually adding a mixture comprising the alpha-aminoalkylenecarboxylic acid and the acid catalyst to a mixture comprising the P—O—P anhydride moiety comprising compound.

4. The method according to claim 1, the method further comprising, after step a) and before step b):
    adding water to the reaction mixture after completion of the conversion of the alpha-aminoalkylenecarboxylic acid into the alpha-aminoalkylene phosphonic acid or ester thereof;
    bringing the reaction mixture comprising the added water to a temperature of between 20° C. and 100° C.; and
    maintaining the reaction mixture comprising the added water at said temperature for at least 10 minutes.

5. The method according to claim 1, wherein the P—O—P anhydride moiety comprising compound is tetraphosphorus hexaoxide.

6. The method according to claim 5, wherein the tetraphosphorus hexaoxide has a purity of at least 95%.

7. The method according to claim 5, wherein the tetraphosphorus hexaoxide contains less than 1000 ppm elemental phosphorus ($P_4$), expressed in relation to $P_4O_6$.

8. The method according to claim 1, wherein the P—O—P anhydride moiety comprising compound is tetraethylpyrophosphite.

9. The method according to claim 1, wherein the P—O—P anhydride moiety comprising compound is selected from the group consisting of tetraphosphorus hexaoxide, $P_4O_7$, $P_4O_8$, $P_4O_9$, and combinations thereof.

10. The method according to claim 1, wherein the alpha-aminoalkylenecarboxylic acid compound is selected from:
    iminodiacetic acid, N,N-bis(cyanomethyl)-glycine, and N-phosphonomethyliminodiacetic acid.

11. The method according to claim 1, wherein the acid catalyst is a homogeneous Brønsted acid catalyst selected from the group consisting of methanesulfonic acid, trifluoromethanesulfonic acid, acetic acid, trifluoroacetic acid, p-toluenesulfonic acid, hydrochloric acid, phosphorous acid, phosphoric acid and mixtures thereof.

12. The method according to claim 1, wherein the acid catalyst is a heterogeneous Brønsted acid catalyst selected from the group consisting of:
   (i) solid acidic metal oxides, optionally supported onto a carrier material;
   (ii) cation exchange resins selected from the group consisting of copolymers of styrene, ethylvinyl benzene and divinyl benzene, functionalized so as to graft $SO_3H$ moieties onto the aromatic group and perfluorinated resins carrying carboxylic and/or sulfonic acid groups;
   (iii) organic sulfonic, carboxylic and phosphonic Brønsted acids which are substantially immiscible in the reaction mixture at the reaction temperature;
   (iv) an acid catalyst derived from:
      the interaction of a solid support having a lone pair of electrons onto which is deposited an organic Brønsted acid;
      the interaction of a solid support having a lone pair of electrons onto which is deposited a compound having a Lewis acid site; or
      heterogeneous solids functionalized by chemical grafting with a Brønsted acid group or a precursor of the Brønsted acid group; and
   (v) heterogeneous heteropolyacids containing hydrogen, one of phosphorus and silicon, and one of tungsten and molybdenum.

13. The method according to claim 1, wherein the acid catalyst is a Lewis acid catalyst selected from the group consisting of $LiN(CF_3SO_2)_2$, $Mg(OCF_3SO_2)_2$, $Al(OCF_3SO_2)_3$, $Bi(OCF_3SO_2)_3$, $Sc(OCF_3SO_2)_3$, and combinations thereof.

14. The method according to claim 1, wherein the reaction mixture comprises a diluent selected from the group consisting of 1,4-dioxane, toluene, ethylacetate, sulfolane, acetonitrile, 1-ethyl-3-methyl-imidazolium bis(trifluoromethylsulfonyl)imide, and mixtures thereof.

15. The method according to claim 1, wherein the P—O—P anhydride moiety comprising compound is mixed with a mixture of the alpha-aminoalkylenecarboxylic acid and the acid catalyst, at a temperature between 20° C. and 120° C.

16. The method according to claim 1, wherein the reaction mixture, after completion of the mixing in step a), is maintained at a temperature between 20° C. and 100° C. for a period of time comprised between 10 minutes and 72 hours.

17. The method according to claim 1, wherein the obtained alpha-aminoalkylenephosphonic acid is selected from the group consisting of aminomethylphosphonic acid, (N,N-dimethylamino)methylphosphonic acid, phthalimidomethylphosphonic acid, N-phenyl-aminomethylphosphonic acid, N-tosyl-aminomethylphosphonic acid, N-phosphonomethyl glycine, phosphonomethyliminodiacetic acid, 4-morpholinemethylphosphonic acid, 4-amino-4-phosphonobutyric acid, 5-phosphono-2-pyrrolidone, N,N-bis(phosphonomethyl)-6-amino-hexanoic acid, N,N-bis(phosphonomethyl)-4-amino-4-phosphono-butyric acid, N,N-bis(phosphonomethyl)-4-amino-glutamic acid, N,N-bis(phosphonomethyl)-1-amino-ethyl-phosphonic acid, imino (bismethylenephosphonic acid), N-methyl-imino (bismethylenephosphonic acid), N-benzyl-imino (bismethylenephosphonic acid), aminotrismethylenephosphonic acid, ethylene diamino tetra-(methylene phosphonic acid), trans-1,2-cyclohexyldiaminotetramethylenephosphonic acid, 1,4,7,10-tetraazadodecane-1,4,7, 10-tetramethylenephosphonic acid, and N-methyl-iminodiphosphonic acid.

18. The method according to claim 1, wherein carbon monoxide produced during the conversion of the alpha-aminoalkanecarboxylic acid is recovered from the reaction mixture.

19. The method according to claim 1, wherein a yield of alpha-aminoalkylenephosphonic acid or ester thereof, based on the alpha-aminoalkylenecarboxylic acid, of at least about 80% is achieved.

20. The method according to claim 1, wherein the alpha-aminoalkylenecarboxylic acid is N,N-bis(cyanomethyl)-glycine.

* * * * *